United States Patent [19]

Ueda et al.

[11] Patent Number: 4,871,549
[45] Date of Patent: Oct. 3, 1989

[54] TIME-CONTROLLED EXPLOSION SYSTEMS AND PROCESSES FOR PREPARING THE SAME

[75] Inventors: Yoshio Ueda, Kobe; Takehisa Hata, Muko; Hisami Yamaguchi, Nishinomiya; Satoshi Ueda, Kawanishi; Masateru Kodani, Ikeda, all of Japan

[73] Assignee: Fujisawa Pharmaceutical Co., Ltd., Osaka, Japan

[21] Appl. No.: 884,071

[22] Filed: Jul. 10, 1986

[30] Foreign Application Priority Data

Jul. 19, 1985 [GB] United Kingdom ............... 8518301

[51] Int. Cl.$^4$ .................... A61K 9/16; A61K 9/46
[52] U.S. Cl. .................... 424/494; 424/466; 424/495; 424/497
[58] Field of Search .............. 424/472, 480, 489, 490, 424/494, 495, 499, 466, 497

[56] References Cited

U.S. PATENT DOCUMENTS

| | | | |
|---|---|---|---|
| 4,369,172 | 1/1983 | Schor et al. | 424/480 |
| 4,663,150 | 5/1987 | Panoz et al. | 424/496 X |
| 4,695,467 | 9/1987 | Vemura et al. | 424/489 X |

FOREIGN PATENT DOCUMENTS

| | | |
|---|---|---|
| 0077956 | 5/1983 | European Pat. Off. |
| 1617724 | 3/1972 | Fed. Rep. of Germany |
| 848389 | 10/1939 | France |

*Primary Examiner*—Michael Lusignan
*Attorney, Agent, or Firm*—Oblon, Spivak, McClelland, Maier & Neustadt

[57] ABSTRACT

The invention relates to a Time-Controlled Explosion System in which drug release is caused by explosion of a membrane after a definite time period, said System comprising a preparation in the form of a bead or granule, said preparation comprising a core, a drug, swelling agent and an outer membrane of water-insoluble coating material.

8 Claims, 1 Drawing Sheet

TIME-CONTROLLED EXPLOSION SYSTEMS AND PROCESSES FOR PREPARING THE SAME

This invention relates to the Time-Controlled Explosion Systems and to processes for preparing the same.

For further particulars, this invention relates to the Time-Controlled Explosion Systems which have sectional structures shown in FIGS. 1, 2, 3 and 4, wherein (1) is a seed of sucrose (core), (2) is a drug, (2a) is a core comprising drug, (2b) is a mixture comprising drug and swelling agent, (3) is a swelling agent, and (4) is membrane, respectively. In these systems, the drug begins to release to the explosion of the outer membrane after a definite time period (defined as "lag times") in case that it is placed into the gastro-intestinal tract. By mixing the systems which have different lag times, the oral sustained release preparations with a various release patterns such as repeat pattern (i.e. drug release occurs repeatedly at every definite time), zero-order pattern (i.e. drug release is at uniform rate), reverse first-order pattern (i.e. drug release rate increases according to the passage of time), sigmoid pattern (i.e. drug release rate is slow at initial and last stage and is fast at middle stage) and so on can be obtained. Sustained release preparations can be used to reduce frequency of dosing, to prevent undesirable side effects and to get optimum therapeutic efficiency.

There are many approaches to prepare the sustained release preparations for the above-mentioned objects. For example, there are preparations wherein drugs are compressed with a water-insoluble materials such as waxes and plastics into a tablet form or drug-coated beads or granules are coated with the various water-insoluble coating materials. However, these preparations have disadvantages that the release rate of the drug decreases according to the passage of time, and is influenced by pH of the gastro-intestinal fluid in case that the solubility of the drug is dependent on pH, and furthermore complete drug release from these preparations dose not occur.

An alternative approach is to prepare the sustained release preparation by mixing the granules of the non-sustained granules with the enteric-coated granules which dissolve in the intestine. As to this type of the preparations, there is possibility that the expected efficiency can not be obtained because the release of the drug is often influenced by the conditions of the gastro-intestinal tract such as pH and the emptying rate.

We have carried out various studies in order to overcome the above-mentioned problems and invented a new type of the oral sustained release dosage forms; namely, Time-Controlled Explosion Systems (hereinafter referred to as T.C.E.S.) From the T.C.E.S., the drug is released by a quite novel mechanism which is neither diffusion control nor dissolution control. In case that T.C.E.S. are placed into the gastro-intestinal tract, gastro fluid penetrates through the outer membrane into the T.C.E.S. and swells the swelling agent incorporated into the T.C.E.S. to result in the explosion of the outer membrane. That is, the release of the drug is occurred by explosion of the outer membrane. In case that the form of T.C.E.S. is tablet, drug is released quickly after the explosion of the outer membrane, while in case that the form of T.C.E.S. is beads or granules, drug is released with zero order pattern after a definite lag time because of the time variance of the explosion of the outer membrane in each bead or granule From the extensive studies, it is found that the explosion of the outer membrane is caused by the power of swelling occurred when swelling agent absorbs the fluid. This is the reason why T.C.E.S. are not influenced by the solubility of the dissolution rate of the drug and pH of the gastro-intestinal fluid and the drug is completely released from T.C.E.S. In addition, it is possible to get the sustained release dosage forms with various release patterns by mixing this T.C.E.S. which have different lag times. T.C.E.S. of the present invention have the following advantages; (i) the release rate or pattern is hardly influenced by the solubility or the dissolution rate of the drug, (ii) the release rate or pattern is independent of pH of the dissolution medium, and (iii) the drug is completely released. In addition, the sustained release dosage form with the various release patterns such as repeat, zero-order, reverse first-order pattern, sigmoid pattern and so on can be obtained by mixing the T.C.E.S. which have different lag times. In case that the form of T.C.E.S. is tablet, repeat pattern can be obtained by combining with non-sustained parts. The lag times can be controlled by the sort or amount of the swelling agent and membrane, and the size of T.C.E.S. The suitable form of T.C.E.S. may be, for example, bead, granule and tablet. Both basic drugs and acidic drugs are applied to T.C.E.S. of the present invention. Basic drugs are, for example, Metoclopramide, Sulpiride, Metoprolol tartrate, Tiapride, Zotepine, Cimetidine, etc. Acidic drugs are, for example, Diclofenac, penicillin and cephalosporine antibiotics, etc. Among these drugs, water-insoluble drug like FK235 substance may be converted, for example, into water-soluble solid dispersion composition. This solid dispersion composition is prepared by dispersing said drug into water-soluble polymer [e.g. hydroxypropylmethylcellulose, polyethylene glycol derivatives (e.g. polyethylene glycol 6000, polyethylene glycol 1500, etc.), etc.].

One type of T.C.E.S. of the present invention in which the form is beads or granules can be prepared as follows. Firstly, the drug-coated or drug-comprised beads and granules are prepared by conventional procedures. For example, nonpareil (granule of sucrose; Trademark; prepared by Freund Co., Ltd.) seeds are placed and rolled in centrifugal granuator or blown up by air in fluid bed granulator. Drug is coated on the seeds with spraying binder (e.g. hydroxypropylmethylcellulose, methylcellulose, polyvinylpyrrolidone, sodium alginate, etc.) dissolved in a suitable solvent (e.g. water, ethanol, etc.). An alternative method which makes beads or granules comprising drug, diluents (e.g. sucrose, lactose, mannit and microcrystalline cellulose and the like) and additives used ordinally in this field by conventional procedures is also available.

Next, the swelling agent is coated on the drug-coated or drug-comprised beads and granules by the same procedure described above. The swelling agents used are, for example, disintegrating agent [e.g. low substituted hydroxypropylcellulose, carboxymethylcellulose calcium, Ac-Di-Sol (carboxymethylcellulose sodium; Trademark; prepared by FMC Inc.), Explotab (sodium starch glycolate; Trademark; prepared by Edward Mendell Co., Ltd.), starch, agar, etc.], synthesized polymer, (e.g. polyvinylacetate, polyacrylic acid, acrylate co-polymer, polyethylene glycol, etc.), inorganic salt (e.g. magnesium chloride, calcium sulfate, etc.), organic salt (e.g. sodium carbonate, calcium bicarbonate, etc.), sugar (e.g. d-mannitol, sucrose, glucose, etc.), tartaric acid, albumin, urea, and the like. Low substituted hydroxypropylcellulose is defined as cellulose substituted with hydroxypropyl in which the ratio of hydroxypropoxyl group is 5 to 16 weight percent. The effervescent agents (e.g. mixture of sodium bicarbonate and tartaric acid, etc.) may be used instead of the swelling agents. The number of layer of the drug and the swelling agent are not limited to one respectively in T.C.E.S. That is, several drug layers and several swelling agent layers can be coated alternatively according to the same procedure as described above, if necessary, to get various release patterns. The ratio of the drug and the swelling agent in the beads or granules is preferably 0.1 to 50 and 30 to 80 weight percent respectively, but is not restricted to the above ratio, and can be changed in accordance with the dose or the lag times to be required respectively. Another type of T.C.E.S. of the present invention in which the form is beads or granules can be prepared firstly as follows.

Nonpareil seeds are coated with a mixture of drug and swelling agent by the same procedure as described above. An alternative method which makes beads or granules comprising drug, swelling agent, diluents (e.g. sucrose, lactose, mannit and microcrystalline cellulose and the like) and additives used ordinally in this field by conventional procedures is also available.

The ratio of the drug and the swelling agent in the beads or granules is the same as one exemplified above. Another type of T.C.E.S. of the present invention in which the form is tablet can be prepared firstly according to conventional procedure, for example, by compressing the mixture of drug, swelling agent, diluents and lubricants (e.g. magnesium stearate, etc.). The ratio of the drug and the swelling agent in the tablet is preferably 0.1 to 30 and 10 to 60 weight percent respectively, but is not restricted to the above ratio.

Finally, swelling agent-coated or comprised beads, granules and tablet prepared by the methods described above are coated with the water-insoluble coating material with additives (e.g. talc, polyethylene glycol, silicone, diethylsebakate, and titanium dioxide and the like) to form outer membrane by conventional procedures. For example, the above-mentioned preparations are placed and blown up by air in fluid bed granulator, and then water-insoluble coating material dissolved in a suitable solvent (e.g. ethanol, dichloromethane, etc.) and additivs are coated on the above-mentioned preparations. The water-insoluble coating material used is, for example, ethylcellulose, hydroxypropylcellulose, shellac, polymethylstyrene, polyvinylacetate, polydiethylaminomethylstyrene, dimethylaminoethylmetacrylate-methylmetacrylate acid-co-polymer [e.g. Eudragit E-30D, Eudragit RL, Eudragit RS (Trademarks; prepared by Röhm Pharma Co., Ltd.)] and wax and the like.

Among these water-insoluble coating materials, ethylcellulose is preferable because ethylcellulose membrane is easy to explode when the swelling agent is swelled. The ratio of the water-insoluble coating material for the above-mentioned preparations is preferably 1 to 50 weight percent, but is not restricted to the above ratio, and can be changed in accordance with the lag times to be required. The size of T.C.E.S. of the present invention is preferably 0.5 mm to 20 mm in diameter. To illustrate the effect of T.C.E.S. of the present invention, dissolution test data and absorption test data are shown in the following.

Dissolution Test 1

Test preparations (Drug: Metoclopramide)
Sample A: Preparation disclosed in Example 3 in which the concentration of ethylcellulose is 7.0 weight %
Sample B: Preparation disclosed in Example 3 in which the concentration of ethylcellulose is 14.2 weight %
Sample C: Preparation disclosed in Example 3 in which the concentration of ethylcellulose is 29.4 weight %
Sample D: Preparation disclosed in Reference 1 is which the concentration of ethylcellulose is 5.0 weight %
Sample E: Preparation in which Sample A and Sample C are mixed in the drug concentration ratio of three to one
Sample F: Preparation in which Sample A and Sample C are mixed in the drug concentration ratio of one to one
Sample G: Preparation in which Sample A and Sample C are mixed in the drug concentration ratio of one to three
Sample H: Preparation disclosed in Example 9
Sample I: Preparation disclosed in Example 10
Test method
(I) The pharmacopoeia of Japan 10th edition
   Dissolution method II (Paddle method)
   Dissolution medium: First fluid (pH 1.2) 900 ml, 37° C., 100 r.p.m.
(II) The pharmacopoeia of Japan 10th edition
   Dissolution method II (Paddle method)
   Dissolution medium: Second flluid (pH 6.8) 900 ml, 37° C., 100 r.p.m.
Test result
Dissolution test data are shown in Tables 1, 2, 3, 4 and 5.

TABLE 1

| Test Preparation | Test method | Dissolution rate (%) | | | | | | | | | |
|---|---|---|---|---|---|---|---|---|---|---|---|
| | | 0.5 hr | 1 hr | 1.5 hr | 2 hr | 3 hr | 4 hr | 5 hr | 6 hr | 7 hr | 8 hr |
| Sample A | I | 5 | 63 | 91 | 95 | 98 | 99 | 100 | 100 | 100 | 100 |
| | II | 4 | 54 | 90 | 95 | 98 | 99 | 100 | 100 | 100 | 100 |
| Sample B | I | 0 | 0 | 0 | 4 | 29 | 83 | 99 | 100 | 100 | 100 |
| | II | 0 | 0 | 0 | 3 | 26 | 81 | 99 | 100 | 100 | 100 |
| Sample C | I | 0 | 0 | 0 | 0 | 0 | 8 | 55 | 90 | 99 | 100 |
| | II | 0 | 0 | 0 | 0 | 0 | 6 | 54 | 85 | 96 | 100 |

TABLE 2

| Test Preparation | Test method | Dissolution rate (%) | | | | | | | | | |
|---|---|---|---|---|---|---|---|---|---|---|---|
| | | 0.5 hr | 1 hr | 1.5 hr | 2 hr | 3 hr | 4 hr | 5 hr | 6 hr | 8 hr | 10 hr |
| Sample D | I | 21 | 38 | 49 | 56 | 64 | 68 | 72 | 74 | 78 | 83 |
| | II | 0 | 3 | 5 | 8 | 10 | 12 | 13 | 14 | 18 | 20 |

TABLE 3

| Test Preparation | Test method | Dissolution rate (%) | | | | | | | | | |
|---|---|---|---|---|---|---|---|---|---|---|---|
| | | 0.5 hr | 1 hr | 1.5 hr | 2 hr | 3 hr | 4 hr | 5 hr | 6 hr | 7 hr | 8 hr |
| Sample E | II | 2 | 38 | 68 | 74 | 75 | 76 | 84 | 95 | 99 | 100 |
| Sample F | II | 2 | 30 | 46 | 48 | 49 | 51 | 69 | 87 | 96 | 99 |
| Sample G | II | 1 | 12 | 22 | 24 | 25 | 29 | 47 | 77 | 91 | 98 |

TABLE 4

| Test Preparation | Test method | Dissolution rate (%) | | | | |
|---|---|---|---|---|---|---|
| | | 1 hr | 2 hr | 4 hr | 6 hr | 8 hr |
| Sample H | I | 2 | 20 | 98 | 100 | 100 |
| | II | 0 | 14 | 91 | 99 | 100 |

TABLE 5

| Test Preparation | Test method | Dissolution rate (%) | | | |
|---|---|---|---|---|---|
| | | 1 hr | 1.25 hr | 1.5 hr | 2 hr |
| Sample I | II | 0 | 95 | 98 | 100 |

Dissolution Test 2

Test preparations (Drug: Metoprolol tartrate)
Sample J: Preparation disclosed in Example 8
Sample K: Preparation disclosed in Reference 2 (control)

Test method
Test methods are the same as ones described in Dissolution Test 1.

Test result
Dissolution test data are shown in Table 6.

TABLE 6

| Test Preparation | Test method | Dissolution rate (%) | | | | | | | |
|---|---|---|---|---|---|---|---|---|---|
| | | 0.25 hr | 1 hr | 2 hr | 3 hr | 4 hr | 5 hr | 6 hr | 7 hr |
| Sample J | I | 0 | 1 | 2 | 39 | 67 | 92 | 95 | 100 |
| | II | 0 | 0 | 2 | 20 | 89 | 94 | 99 | 100 |
| Sample K | I | 100 | — | — | — | — | — | — | — |
| | II | 100 | — | — | — | — | — | — | — |

Absorption Test

Test Method
Test preparations (Sample J and Sample K) were administered orally to three Beagle dogs weighing about 10 kg that were fasted overnight respectively.

Dose of each test preparation was 120 mg as Metoprolol tartrate. 0.5, 1, 2, 4, 6, 8 and 10 hours after oral administration, blood was collected into a heparinized tube. After centrifuging, plasma concentrations of Metroprolol were measured by high pressure liquid chromatography.

Test result
Test result is shown in Table 7. Plasma concentration was shown by mean-value of three dogs.

TABLE 7

| Test Preparation | plasma concentration (ng/ml) | | | | | | |
|---|---|---|---|---|---|---|---|
| | 0.5 hr | 1 hr | 2 hr | 4 hr | 6 hr | 8 hr | 10 hr |
| Sample J | N.D. | N.D. | 61 | 479 | 294 | 172 | 109 |
| Sample K (control) | 519 | 752 | 736 | 412 | 150 | 112 | 79 |

(N.D.: plasma concentration was not detected)

Release patterns of the T.C.E.S. of the present invention in which the drug and the swelling agent are separated are shown in Table 1. These data show that the drug begins to release after a definite time and the drug is completely released with the zero-order pattern after the sample is subjected to the dissolution test.

As shown in Table 1, the lag times increase with the membrane thickness. In addition, the release rate and pattern is independent of pH, whereas, as shown in Table 2, the drug containing beads coated with the membrane in the absence of the swelling agent (Sample D) give the release rate which is dependent on pH of the dissolution medium and the drug is not completely released from this beads even after 10 hours, though the membrane is thinner than the above T.C.E.S. of the present invention (i.e. Samples A to C).

The representative release patterns of the drug from the mixture of Sample A and Sample C are shown in Table 3.

As apparent from Table 3, T.C.E.S. of the present invention provide for the new type of the oral sustained release preparations in which the release rate and pattern are freely controlled.

Release pattern of the another type of T.C.E.S. of the present invention in which drug and swelling agent are mixed is shown in Table 4.

Release pattern is almost the same as ones of T.C.E.S. as stated above in which the drug and the swelling agent are separated.

Release pattern of the T.C.E.S. in which the preparation form is tablet is shown in Table 5.

As shown in Table 5, drug is released quickly from this type of T.C.E.S. after a definite lag time. Absorption test data are shown in Table 7. These data show that plasma concentration of Metoprolol is not detected until 1 hour, slightly detected at 2 hour and is attained to maximum at 4 hour after oral administration of T.C.E.S. of the present invention (Sample J), whereas high plasma concentration is detected at 0.5 hour after oral administration of Sample K (control).

This absorption test data reflects the dissolution test data shown in Table 6; namely, Metoprolol is not released until 1 hour, slightly released at 2 hour and mostly released at 4 hour from T.C.E.S. of the present invention (Sample J).

These data suggest that sustained plasma concentration can be obtained by mixing T.C.E.S. which have different lag time, for example, shown in Table 1.

As mentioned above, the T.C.E.S. of the present invention have many excellent advantages and have solved many problems of the prior arts.

The present invention is illustrated according to the examples as shown below, but is not limited thereto. The chemical names and formulae of the drugs in the examples are shown below.

(i) Chemical name:
2-methoxy-4-amino-5-chloro-N-(β-diethylaminoethyl)-benzamide (Metoclopramide)

Formula;
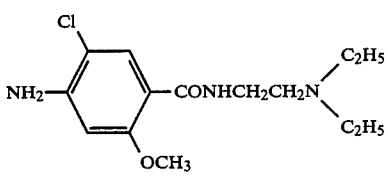

(ii) Chemical name:
N-[2-(diethylamino)ethyl]-5-(methylsolfonyl)-o-anisamide hydrochloride (Tiapride)

Formula;
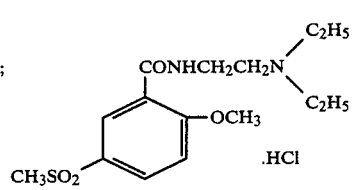

(iii) Chemical name: 5-isopropyl 3-methyl 2-cyano-1,4-dihydro-6-methyl-4-(m-nitrophenyl)-3,5-pyridinedicarboxylate (FK235 substance)

Formula;
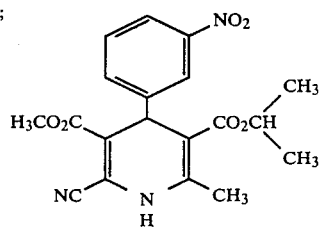

(iv) Chemical name:
`dl-1-(isopropylamino)-3-[p-(2-methoxyethyl)phenoxy]-2-propanol hemi-L-tartrate (Metoprolol tartrate)

Formula;
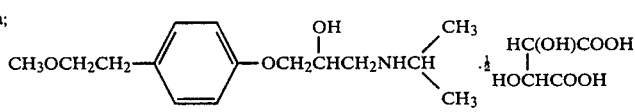

EXAMPLE 1

Nonpareil seeds (2 kg) were placed and rolled in a centrifugal granulator. Metoclopramide (670 g) was coated on said Nonpareil seeds with spraying hydroxypropylmethylcellulose (36 g) dissolved in water (720 g).

EXAMPLE 2

The drug-coated beads (1.05 kg) prepared in Example 1 were placed and rolled in a centrifugal granulator. Low substituted hydroxypropylcellulose (1.65 kg) was coated on said beads with spraying hydroxypropylmethylcellulose (0.209 kg) dissolved in ethanol-water mixture (85:15 V/V %) (4.18 l).

EXAMPLE 3

The swelling agent-coated beads (100 g) prepared in Example 2 were placed and blown up with air in a fluid bed granulator. Ethylcellulose dissolved in ethanol and talc was sprayed to coat on said beads to give the desired preparations. Three preparations wherein the concentration of ethylcellulose is 7.0, 14.2 and 29.4 weight % for the beads prepared in Example 2 were prepared.

EXAMPLE 4

Time-Controlled Explosion System, wherein core is Nonpareil seed (420 g), drug is Metoclopramide (140 g), swelling agent is Explotab (840 g) and water-insoluble coating material contains ethylcellulose and talc, was prepared according to similar procedures to those of Examples 1, 2 and 3. The concentration of ethylcellulose for the beads prepared according to a similar procedure to that of Example 2 is 17.7 weight %.

EXAMPLE 5

Time-Controlled Explosion System, wherein core is Nonpareil seed (420 g), drug is Metoclopramide (140 g), swelling agent is Ac-Di-Sol (840 g) and water-insoluble coating material contains ethylcellulose and talc, was prepared according to similar procedures to those of Examples 1, 2 and 3. The concentration of ethylcellulose for the beads prepared according to a similar procedure to that of Example 2 is 21.8 weight %.

EXAMPLE 6

Time-Controlled Explosion System, wherein core is Nonpareil seed (778 g), drug is Tiapride (158 g), swelling agent is low substituted hydroxypropylcellulose (870 g) and water-insoluble coating material contains ethylcellulose and talc, was prepared according to similar procedures to those of Examples 1, 2 and 3. The concentration of ethylcellulose for the beads prepared according to a similar procedure to that of Example 2 is 21.2 weight %.

EXAMPLE 7

FK235 substance (2 g) was dissolved in a mixture of polyethylene glycol 1500 and polyethylene glycol 6000 (1:1 W/W) (100 g) with heating. After cooling, granules which contain FK235 substance were prepared according to the conventional method. Thereafter, Time-Controlled Explosion System, wherein swelling agent is low substituted hydroxypropylcellulose (500 g) and water-insoluble coating material contains ethylcellulose and talc, was prepared according to similar procedures to those of Examples 2 and 3. The concentration of ethylcellulose for the granules prepared according to a similar procedure to that of Example 2 is 10.5 weight %.

EXAMPLE 8

Time-Controlled Explosion System, wherein core is Nonpareil seed (392 g), drug is Metoprolol tartrate (168 g), swelling agent is low substituted hydroxypropylcellulose (840 g) and water-insoluble coating material contains ethylcellulose and talc, was prepared according to similar procedures to those of Examples 1, 2 and 3. The concentration of ethylcellulose for the beads prepared according to a similar procedure to that of Example 2 is 12.65 weight %.

EXAMPLE 9

Nonpareil seeds (500 g) were placed and rolled in a centrifugal granulator. Metoclopramide (170 g) and low substituted hydroxypropylcellulose (1000 g) were mixed and the mixture was coated on said nonpareil seeds with spraying hydroxypropylmethylcellulose (150 g) dissolved in ethanol-water mixture (85:15 V/V %) (3 l). Ethylcellulose dissolved in ethanol and talc was sprayed to coat on the seeds as obtained to give Time-Controlled Explosion System. The concentration of ethylcellulose for the beads as obtained is 13.2 weight %.

EXAMPLE 10

Metoclopramide (7.7 g), lactose (42 g), microcrystalline cellose (30 g), Ac-Di-Sol (20 g) and magnesium stearate (0.3 g) were mixed and the mixture was compressed into tablets. Ethylcellulose dissolved in ethanol was sprayed to coat on said tablets to give Time-Controlled Explosion System.

|  |  |
|---|---|
| Metoclopramide | 7.7 mg |
| lactose | 42 mg |
| microcrystalline cellulose | 30 mg |
| Ac-Di-Sol | 20 mg |
| magnesium stearate | 0.3 mg |
| ethylcellulose | 5.2 mg |
|  | 105.2 mg |

Reference 1

For the purpose of comparing with the preparation prepared in Example 3, Metoclopramide beads (105 g) coated with ethylcellulose without swelling agent were prepared according to similar procedures to those of Examples 1 and 3 without the process described in Example 2. The concentration of ethylcellulose for the Metoclopramide beads is 5.0 weight %.

Reference 2

For the purpose of comparing with the preparation prepared in Example 8, Metoprolol tartarte beads (560 g) without swelling agent and water-insoluble coating material were prepared according to a similar procedure to that of Example 1.

Brief description of the drawings are as follows.

Figure 1:
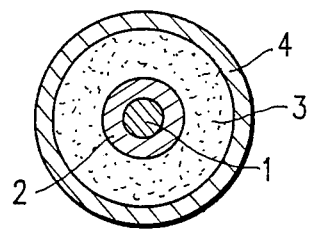
FIG. 1 shows a sectional structure of T.C.E.S. disclosed in Examples 3 to 6 and 8 in which (1) is a seed of sucrose (core), (2) is a drug, (3) is a swelling agent and (4) is membrane respectively.
Figure 2:
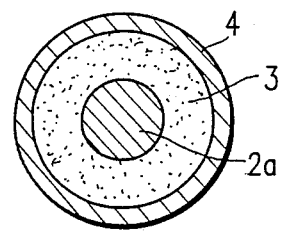
FIG. 2 shows a sectional structure of T.C.E.S. disclosed in Example 7 in which (2a) is a core comprising drug (3) is a swelling agent and (4) is membrane respectively.
Figure 3:
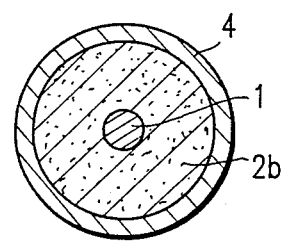
FIG. 3 shows a sectional structure of T.C.E.S. disclosed in Example 9 in which (1) is a seed of sucrose (core), (2b) is a mixture comprising drug and swelling agent and (4) is membrane respectively.
Figure 4:
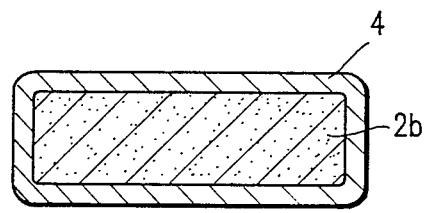
FIG. 4 shows a sectional structure of T.C.E.S. disclosed in Example 10 in which (2b) is a mixture comprising drug and swelling agent and (4) is membrane respectively.

What we claim is:

1. A Time-Controlled Explosion System in which drug release is caused by explosion of a membrane after a definite time period, said System comprising a preparation in the form of a bead or granule, said preparation comprising a core which is covered with an outer layer of drug, a further outer layer of disintegrating agent or synthesized polymer selected from the group consisting of polyvinylacetate and polyacrylic acid, and an outer membrane of a water-insoluble coating material.

2. A Time-Controlled Explosion System in which drug release is caused by explosion of a membrane after a definite time period, said System comprising a preparation in the form of a bead or granule, said preparation comprising a core of a drug which is covered with an outer layer of disintegrating agent of synthesized polymer selected from the group consisting of polyvinylacetate and polyacrylic acid, and an outer membrane of a water-insoluble coating material.

3. A Time-Controlled Explosion System in which drug release is caused by explosion of a membrane after a definite time period, said System comprising a preparation in the form of a bead or granule, said preparation comprising a core which is covered with an outer layer of the mixture of drug and disintegrating agent of synthesized polymer selected from the group consisting of polyvinylacetate and polyacrylic acid, and an outer membrane of a water-insoluble coating material.

4. A Time-Controlled Explosion System according to any one of claims 1 to 3, wherein the water-insoluble coating material comprises ethylceluose.

5. A Time-Controlled Exposion System according to any one of claims 1 to 3, wherein the disintegrating agent is low substituted hydroxypropylcellulose, sodium starch glycolate or carboxymethylcellulose sodium.

6. A Time-Controlled Explosion System according to any one of claims 1 to 3, characterized in mixing systems which have different lag times to obtain sustained release preparations with various release patterns.

7. A method for preparing a Time-Controlled Explosion System in which drug release is caused by the explosion of a membrane after a definite time period characterized in that after preparing beads or granules comprising a drug, a disintegrating agent or synthesized polymer selected from the group consisting of polyvinylacetate and polyacrylic acid is firstly coated thereon, and then a water-insoluble coating material is further coated thereon.

8. A method for preparing a Time-Controlled Explosion System in which drug release is caused by the explosion of a membrane after a definite time period characterized in that after preparing beads or granules comprising a drug and disintegrating agent or synthesized polymer selected from the group consisting of polyvinylacetate and polyacrylic acid, a water-insoluble coating material is coated thereon.

* * * * *